Figure 1:
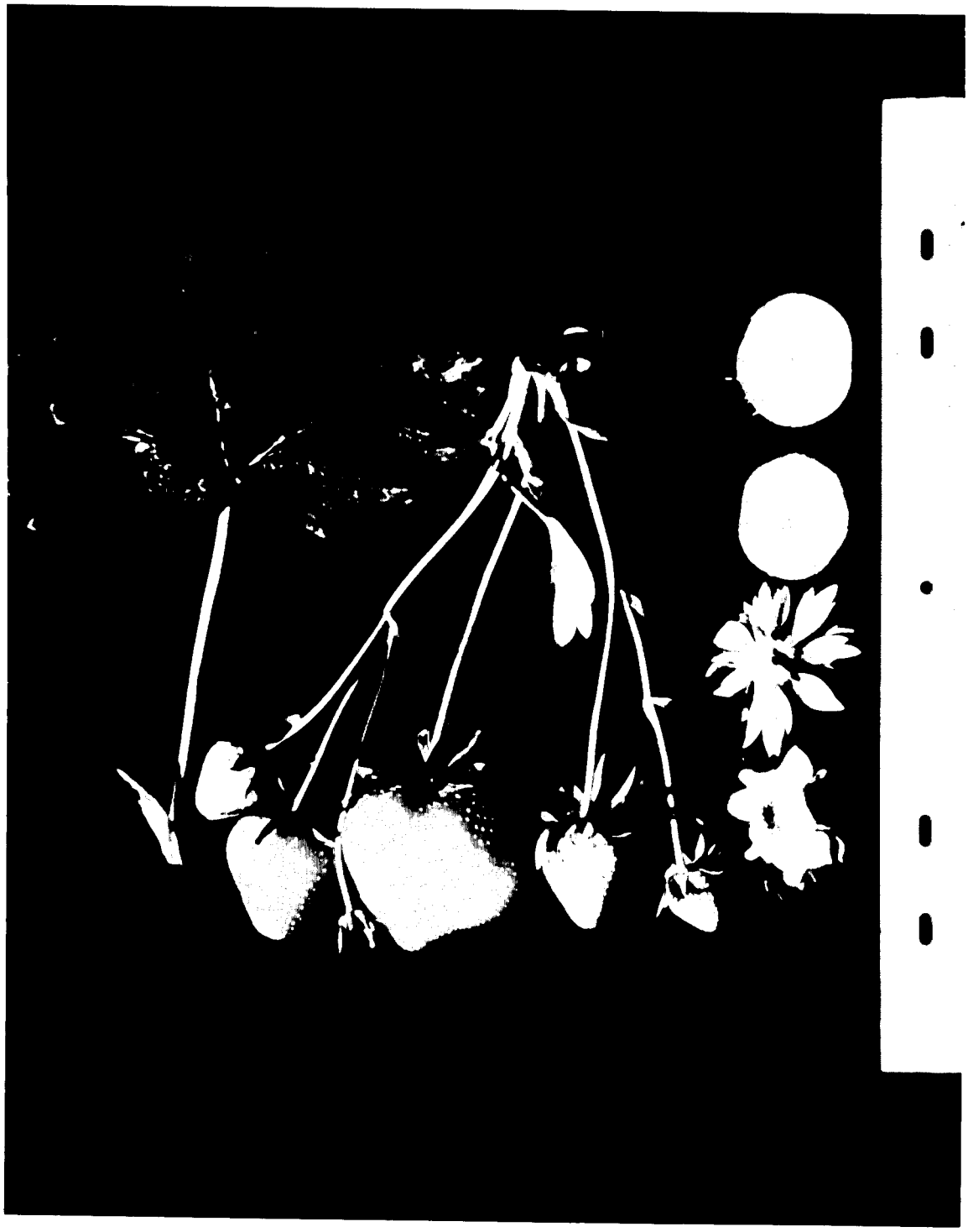

United States Patent [19]
Johnson, Jr.
[11] Plant 4,574
[45] Jul. 15, 1980

[54] STRAWBERRY PLANT

[75] Inventor: Harold A. Johnson, Jr., Watsonville, Calif.
[73] Assignee: Driscoll Strawberry Associates, Inc., Watsonville, Calif.

[21] Appl. No.: 27,195
[22] Filed: Apr. 4, 1979
[51] Int. Cl.³ ..... A01H 5/03
[52] U.S. Cl. ..... Plt./48
[58] Field of Search ..... Plt./48

*Primary Examiner*—Robert E. Bagwill

[57] ABSTRACT

A new and distinct variety of strawberry plant characterized in having deep serrations at the leaflet margins, especially during summer growth; the plant crops early in spring following summer planting. The primary fruit is large medium wedge in shape and is distinguished by its strong sweet flavor and noticeable aroma.

1 Drawing Figure

1

This variety relates to a new and distinct variety of strawberry plant known as H-8 and which is the result of a cross of the Driscoll Strawberry Associates patent No. 2,892 (F-5) and Driscoll Strawberry Associates unpatented selection G-8.

The seedlings resulting from the aforementioned cross were grown and asexually multiplied by runners in Shasta County, Calif. and tested in the fruiting beds on the property of member growers of Driscoll Strawberry Associates, Inc. Clones of the seedlings were also held at the Propagation Nursery in Shasta County. One plant was selected from the aforementioned group of seedlings and further asexually reproduced in the Shasta County Nursery of Driscoll Strawberry Associates, Inc. Tests followed in various parts of California during intervening seasons on various properties of grower members of the Driscoll Strawberry Associates, Inc. These tests indicated the merits of the novel plant and resulted in its selection as a promising test variety.

FIG. 1 of the accompanying drawing illustrates plant parts of the new variety, typical in size, shape and color in Oxnard, Calif. during April.

A berry shown in cross section illustrates flesh color and characteristic core cavity. The serrated sepals in the calyx shown are typical early in the season and aren't clasping and may become reflexed later in the season. The anthers on the flowers are mature and produce an abundance of pollen even early in the spring. The inflorescence pictured illustrates typical branching during early spring with the pedicel holding the primary berry originating from the axil of secondary peduncles, but the pedicel often originates from one of the secondary peduncles. The strong pedicel holding a primary berry is typical, as is the large medium wedged primary fruit early in the spring, both in southern California and in the central coast area. The leaf shown is typical early in the spring and is darker than subsequent leaves and the petiole becomes longer later in the season. The deep serrations at the leaflet margins are typical and are deep and distinct, especially during summer growth.

The novel new summer planted spring variety appears to be adapted to both southern and central California. One of its distinct attributes is its strong sweet flavor which makes it rate high during ratings made by test panelists. It also is distinct in that it crops very early in the spring following a late summer planting. This earliness has to be manipulated by planting dates or cropping occurs prematurely. When properly grown

2 this cropping commences in Oxnard during mid-March and late April in central California.

The plant of this variety is medium to large if cultural farming practices have been adequate. It becomes taller, but not denser than Driscoll's H4, U.S. Plant Pat. No. 3,987. The leaflets and foliage are usually lighter in color and individual leaflets are larger, with less pubescence, and the serrations at leaflet margins are deeper and more noticeable than that of H4. The petiolule of the new variety is generally not as long as that of H4. Mature plants usually have fewer crowns than H4, but individual crowns have a greater diameter. Individual petioles are longer and thicker than those of H4.

The berry size is generally larger, the shape tends to be more often wedged, the color is lighter, the flavor is sweeter and there is a more noticeable odor to the new variety than H4. The fruit firmness appears to equal H4 even though the seed is not as exerted as H4. Late in the year the epidermis is less susceptible to injury than H4. The fruit surface is light in color, lighter and more prone to a light colored tip or apex than H4. The cropping of the new variety is considerably earlier, but not as consistent throughout the year and has more runners during the fruiting year than H4. The new variety appears to be quite susceptible to injury from thrip, causing an objectionable bronzing appearance to the fruit. The foliage is prone to injury from the miticide Plictran, when grown and sprayed under greenhouse conditions. This characteristic is a distinct marker when comparing it with other varieties.

Based on natural field infection from *Phytophthora fragariae* (Red Stele) in Watsonville this new variety has a degree of tolerance. This new variety is a strong runner producer at the nursery and is also prone to runnering after the spring crop. It doesn't produce more plants per acre at the nursery than H4, but individual plants have a larger diameter crown than H4. The new variety has had limited exposure to Mycospharella leafspot and mildew but it appears to equal in susceptibility to these organisms as H4. Leafspot infection from the fungus alternaria has been observed in southern California. It is more susceptible to the two-spotted mite than H4 the spring following a summer planting if the planting date occurred the same time as H4.

As a seedling and selection, this new variety withstood the natural invasion of certain virus components found in central and southern California.

The varietal characteristics of the novel plant, described below in detail, were observed mainly during the first fruiting season during the late spring and summer in central California, but observations already described were made earlier in the fruiting season both in southern and central coastal California. The color terminology as used herein is in accordance with Ridgeway's Color Standards and Nomenclature (1912 Edition).

Plants:

*Medium in early spring following summer planting-*.—Becoming large during late spring and summer. Transplants are large as they come from the propagation nursery. It has an extensive root system.

Leaflets:

*Large in size.*—Mature central leaflets 8 to 10 cm. in length and width. Petioles are strong and heavy, bracts on the petioles may or may not be present. One or two funnel-shaped leaflets may also be present, plus the normal three leaflets. Serrations at leaflet margins are noticeably deep. Color of upper side of leaflet is Ivy Green, Plate XXXI.

Isozymes in leaf extracts — *Phosphoglucose isomerase* (PGI): New variety gave a slow, three banded pattern similar to "Tufts," a University of California introduction, with the provisional monohybrid genotype of 30/35 35/35 35/35 35/35 mm. (Scandalios. 1969 Biochem. Genet. 3:37-79).

Runners: Runners are vigorous and abundant, both at nursery and fruiting beds.

Inflorescence:

*Medium to long in length.*—But common peduncle may be lacking during early spring, but is present during late spring and summer crops. Pedicel holding primary berry may originate from the axil of two peduncles or originate from one of the peduncles. Hair on tertiary pedicels 20 mm. from the berry are irregularly parallel. Flowers produce anthers with an abundance of pollen even during early spring.

Fruit:

*Primaries.*—From first crop are large and maintain good size if plant vigor is adequate to support crop. Primaries are medium wedge in outline, but secondaries and tertiaries mostly conic, as described in USDA Bulletin 1043. Primaries 40 to 50 mm. in length and width. Shoulders of fruit near calyx are rounded not necked, but it is not uncommon to produce an epidermis void of seed near the calyx, giving a slight reflex appearance. The fruit surface is generally smooth with a minimum of ridging or irregular shaped fruit, giving the fruit an attractive appearance when bronzing due to thrip injury doesn't occur. Seed is held equal to fruit surface, to slightly exerted. The core is medium. The flesh and epidermis is firm, especially during periods when the plant isn't dense. The flavor is sweet to the taste and rates consistently high during taste panel tests. The surface color is Spectrum Red, Plate I, and the flesh color is Scarlet, Plate I. The fruit have a noticeable strawberry aroma.

Calyx:

*Medium to large.*—In diameter with large serrated sepals, especially early in the fruiting season. During summer and fall the calyx is not as large in relationship to fruit size and serrations of sepals not as abundant. During summer and fall the calyx may be reflexed. The color of sepals on the side facing the fruit is Light Cress Green, Plate XXXI.

Seed:

*Medium in size.*—Abundant and evenly spaced. Yellow but becoming dark when exposed to full sun.

I claim:

1. The new and distinct variety of strawberry plant herein described and illustrated, and identified by the characteristics enumerated above.

* * * * *